United States Patent

Kažys et al.

[11] Patent Number: 5,847,281
[45] Date of Patent: Dec. 8, 1998

[54] SYSTEM FOR MEASURING ULTRASONICALLY THE ELASTIC PROPERTIES OF A MOVING PAPER WEB

[75] Inventors: Rymantas J. Kažys, Kaunas, Lithuania; T. Patrick Stolpe, Alunda, Sweden

[73] Assignee: AB Lorentzen & Wettre, Kista, Sweden

[21] Appl. No.: 809,102

[22] PCT Filed: Oct. 5, 1995

[86] PCT No.: PCT/SE95/01144

§ 371 Date: Mar. 26, 1997

§ 102(e) Date: Mar. 26, 1997

[87] PCT Pub. No.: WO96/11395

PCT Pub. Date: Apr. 18, 1996

[30] Foreign Application Priority Data

Oct. 6, 1994 [SE] Sweden ................................... 9403383

[51] Int. Cl.⁶ .......................... G01N 29/08; G01N 29/18; G01N 29/24
[52] U.S. Cl. .......................... 73/597; 73/159; 364/469.01
[58] Field of Search .......................... 73/597, 159, 644, 73/639; 364/550, 469.01; 162/198, 263

[56] References Cited

U.S. PATENT DOCUMENTS

| | | | |
|---|---|---|---|
| 3,720,098 | 3/1973 | Dixon | 73/597 |
| 4,291,577 | 9/1981 | Baum et al. | 73/159 |
| 4,446,735 | 5/1984 | Weilacher | 73/597 |
| 4,574,634 | 3/1986 | Pappano | 73/597 |
| 4,688,423 | 8/1987 | Orkosalo | 73/159 |
| 4,730,492 | 3/1988 | Burk | 73/159 |
| 4,735,087 | 4/1988 | Hourani et al. | 73/597 |
| 5,014,547 | 5/1991 | Holroyd | 73/105 |
| 5,025,665 | 6/1991 | Keyes, IV et al. | 73/159 |
| 5,398,538 | 3/1995 | Williams et al. | 73/1 DV |
| 5,525,854 | 6/1996 | Hall et al. | 310/334 |

FOREIGN PATENT DOCUMENTS

| | | |
|---|---|---|
| 489018 | 6/1974 | U.S.S.R. . |
| 489036 | 6/1974 | U.S.S.R. . |
| WO 91/17435 | 11/1991 | WIPO . |

*Primary Examiner*—Hezron E. Williams
*Assistant Examiner*—Rose M. Miller
*Attorney, Agent, or Firm*—Burns, Doane, Swecker & Mathis, L.L.P.

[57] ABSTRACT

An arrangement for ultrasonically measuring the elastic properties of a moving web includes an ultrasonic wave generator and at least two ultrasonic wave detection devices which receive the generated ultrasonic wave without contacting the web. The received signal is processed such that the desired properties if the moving web can be determined.

15 Claims, 6 Drawing Sheets

SYSTEM FOR MEASURING ULTRASONICALLY THE ELASTIC PROPERTIES OF A MOVING PAPER WEB

This invention concerns the measurement of the velocity of ultrasound, in-plane, for a moving paper web. The ultrasound velocity in paper is known to be related to various measures of paper strength and stiffness.

BACKGROUND OF THE INVENTION

The most important values for the papermaker to consider from ultrasound velocity measurements on a paper web are:

TSO Tensile Stiffness orientation, i.e. the orientation of the elastic properties in-plane of the paper sheet, $TSI_{MD}$ Tensile Stiffness Index in the machine direction of the paper machine, $TSI_{CD}$ Tensile Stiffness Index in the cross direction of the paper machine.

It is possible to determine these quantities and also the anisotropy ratio $TSI_{MD}/TSI_{CD}$ by performing the ultrasound velocity measurements in the machine direction (MD), cross direction (CD), and directions between (MD) and (CD). The tensile stiffness and anisotropy ratio characterize the paper quality.

The velocity of an ultrasonic pulse propagating in-plane of a paper sheet corresponds with the sheet's elastic properties, i.e. the TSI. TSI can be compared to Young's modulus (or "E-modulus") for other materials. The relationship can be expressed by:

ti $TSI=v^2*c$ where TSI is measured in kNm/g, v is the propagation velocity (km/sek) for the ultrasonic pulse, and c is a dimensionless constant close to 1 depending on Poisson's ratio for the paper. The velocity is easily determined by measuring the propagation time for an ultrasonic pulse between a transmitter and a receiver.

These quantities are often measured statically on samples taken from a paper web. However it is desirable to measure these paper quantities on-line by an on-line meter used as a sensor for the continuous control of a paper manufacturing process.

Most of the known on-line meter arrangements (U.S. Pat. No. 4,291,577, U.S. Pat. No. 4,688,423, U.S. Pat. No. 4,730,492) employ rotating wheels, which contain transmitters and receivers of ultrasonic waves. These wheels are rotated by a moving paper web, which requires a direct physical contact between the wheels and the web. The ultrasound velocity is usually determined from the delay time of an ultrasonic signal between the particular transmitter and receiver.

In order to obtain a reasonable measurement accuracy, the wheels must be synchronized which makes the system extremely complicated and unreliable. An arrangement described in U.S. Pat. No. 4,688,423 overcomes this drawback by exploying disk type transducers which can be excited continuously and, therefore, synchronization of the wheels is not necessary. However, the arrangements described in the above-mentioned patent specifications need a direct mechanical contact between the ultrasonic transducers and the web.

In a papermaking machine the fast moving web vibrates in the direction normal to the web surface, creating a randomly changing force applied to the wheels. The amplitude of excited and received ultrasonic waves depends on the pressure between particular ultrasonic transducer and the web. Due to the randomly changing force, the amplitudes of received signals fluctuate, thereby making the results of measurements less accurate.

The physical contact with the web is not needed if ultrasonic waves are excited and detected optically, as described in U.S. Pat. No. 5,025,665. Ultrasonic waves in the paper web are generated by means of a laser. This wave is detected at a determined distance from the excitation point by means of another laser beam, reflected from the web. The velocity of the ultrasonic wave is found from the measured delay time between the excitation instant and the time of the wave arrival.

The disadvantage of this optical system is that the amplitudes of the ultrasonic waves propagating in-plane of the web are very small. A very strong acoustic noise exists in papermaking machines, which is accompanied by the vibrations of the moving web. In fact this makes the optical detection of the lowest orders symmetrical Lamb waves impossible, and only these waves are suitable for the stiffness and tensile strength measurements of paper.

A method and device for continuously determining the modulus of elasticity of advancing flexible material, such as paper web, in a contactless fashion is disclosed in WO91/17435. An ultrasonic wave train is transmitted through the air towards the web. FIG. 6 shows an embodiment in which the ultrasonic waves scattered through the air by the material are sensed both at a distance d and at a distance d' at the same side of the web, no reference ultrasonic wave receiving means being provided for receiving a reference ultrasonic wave from the transmission point. The measured distance is between the two pick-up ultrasonic wave receiving means, thus not between the position where the ultrasonic wave is generated and the position of the pick-up ultrasonic wave receiving means.

Other prior on-line paper measuring systems are disclosed in the U.S.S.R. Pat. No. 489018 and U.S.S.R. Pat. No. 489036, and described in the publication by Kazys (the same inventor as for the present invention), Proceedings of 20th international conference on Acoustics, Prague, 1981, pp. 6–10. The ultrasound velocity in a moving paper web was determined by exciting broad band noise-like ultrasonic wave by means of a dry friction, receiving the ultrasonic wave reradiated by the web by two non-contacting ultrasonic receivers and calculating cross-correlation function between these two received signals. The first receiver was placed opposite to the ultrasonic transmitter and the second a determined distance from the transmitter along the web.

In order to improve signal/noise ratio, a rotating cylinder was placed underneath the web close to the second ultrasonic receiver. The delay time was determined from the delay of the peak value of the cross-correlation function. The advantage of this measuring system compared to the ones described above was that it had no moving or rotating parts.

The disadvantage of the system described in the above-mentioned USSR-patents is that the signal/noise ratio is not sufficiently high enough to permit reliable continous on-line measurements in a mill environment. Another disadvantage is that excitation and reception of the ultrasonic waves are performed from the opposite sides of the paper web. Another problem which is encountered in performing measurements in other directions than the machine direction (MD) is that an even worse signal/noise ratio is then obtained due to the higher losses of ultrasonic waves in an anisotropic material.

The main object of the invention is to provide improved noise robustness for the system in a paper mill environment.

Another object of the invention is on-line measuring system with single side access to the paper web, performing measurements at different directions in-plane of a moving web.

Still another object of the invention is to provide an improved signal processing method for reliable determination of the ultrasound velocity in the paper web.

SUMMARY OF THE INVENTION

The present invention solves the problems associated with the prior art and other problems by providing a system for continuous measurement of the velocity of ultrasonic waves in a moving paper web. The foregoing is accomplished by exciting a ultrasonic wave, such as broad-band noise type Lamb wave in the web, receiving the ultrasonic wave reradiated by the web at least at three different points without contacting the web, and determining the delay time between the received signal, received directly by a first reference receiver microphone placed in the vicinity of the excitation point, and two other added signals, received by pick-up receiver microphones separated by a half-wavelength in air of the transmitted ultrasonic wave at the center frequency of the frequency band used for measurements.

The distances between the excitation point and the two pick-up receivers is known. The delay time of the ultrasonic wave is preferably determined as a zero cross of the Hilbert transform of the cross-correlation function of the received signals, corresponding to the maximum value of the cross-correlation function. The source of ultrasonic waves and all the ultrasonic receivers are preferably located on only one side of the web.

In order to make the system noise robust, i.e. provide a low signal/noise ratio, the receiving of the reradiated ultrasonic waves is performed above a rotating cylinder in a paper making machine at the particular position in respect to the line, where the moving web touches the cylinder for the first time. The broad band noise-like Lamb wave in the web is generated by means of dry friction contact between the moving web and a friction head. Therefore, the system has no moving parts and all signals are received by non-contacting means.

BRIEF DESCRIPTION OF THE DRAWINGS

For a more complete understanding of the present invention and for further objects and advantages thereof, reference is now made to the following description taken in conjunction with the accompanying drawings, in which:

With reference to FIG. 1, a prior art on-line paper measuring system disclosed in the.U.S.S.R. Pat. No. 489018 includes a friction head 1 provided on one side of a moving paper web 2 and generating a noise-like ultrasonic signal $v_w$ as a result of dry friction between the head 1 and the web 2. A random signal with a normal law of distribution up to 70 to 90 kHz is excited. The part of this signal $v_w$ propagating in the paper web 2 as the zero order symmetrical Lamb wave $s_0$ is the interesting one to examine. The excited wave is reradiated partially into the surrounding air and is picked up by a contactless reference microphone Mic 1 provided opposite the head 1 on the other side of the web 2, and by a contactless pick-up microphone Mic2 provided on the same side of the web as the reference microphone Mic1 but a determined distance away from, i.e. downstream from, the head 1 along the web in its moving direction, below called "the machine direction". In order to have an enhanced reradiation of the propagated wave from the web to the air the web 2 is supported by a rotating cylinder 3 opposite the pick-up microphone Mic2. The signals from the microphones Mic1 and Mic2 are fed to a processing unit 4', which correlates the two signals in order to derive the propagation time through the web, so that the velocity of the ultrasonic wave in the paper web can be computed and the result presented on a display 5'.

Figure 1:
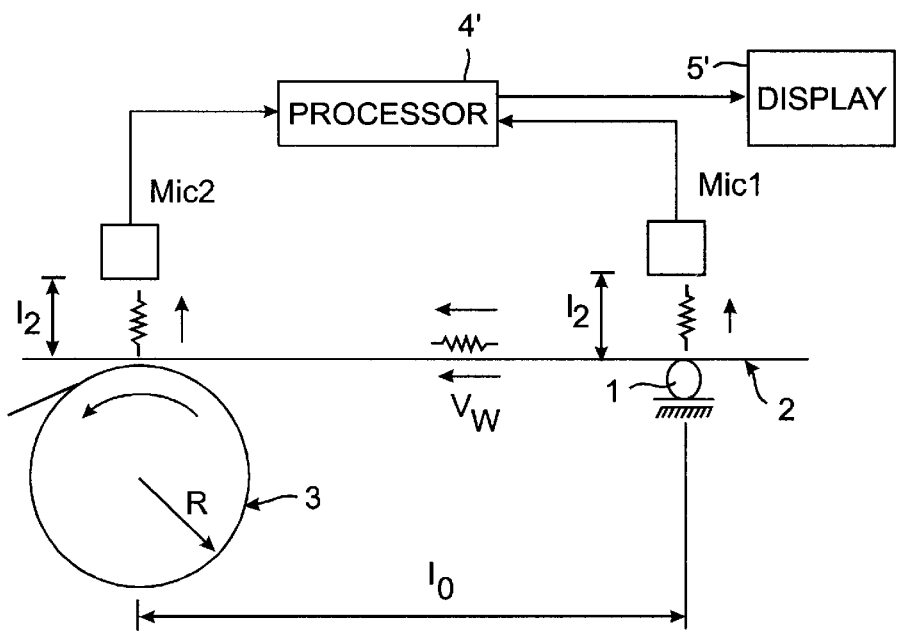
FIG. 1 is a schematic side view of a measuring system according to the prior art.
Figure 2:
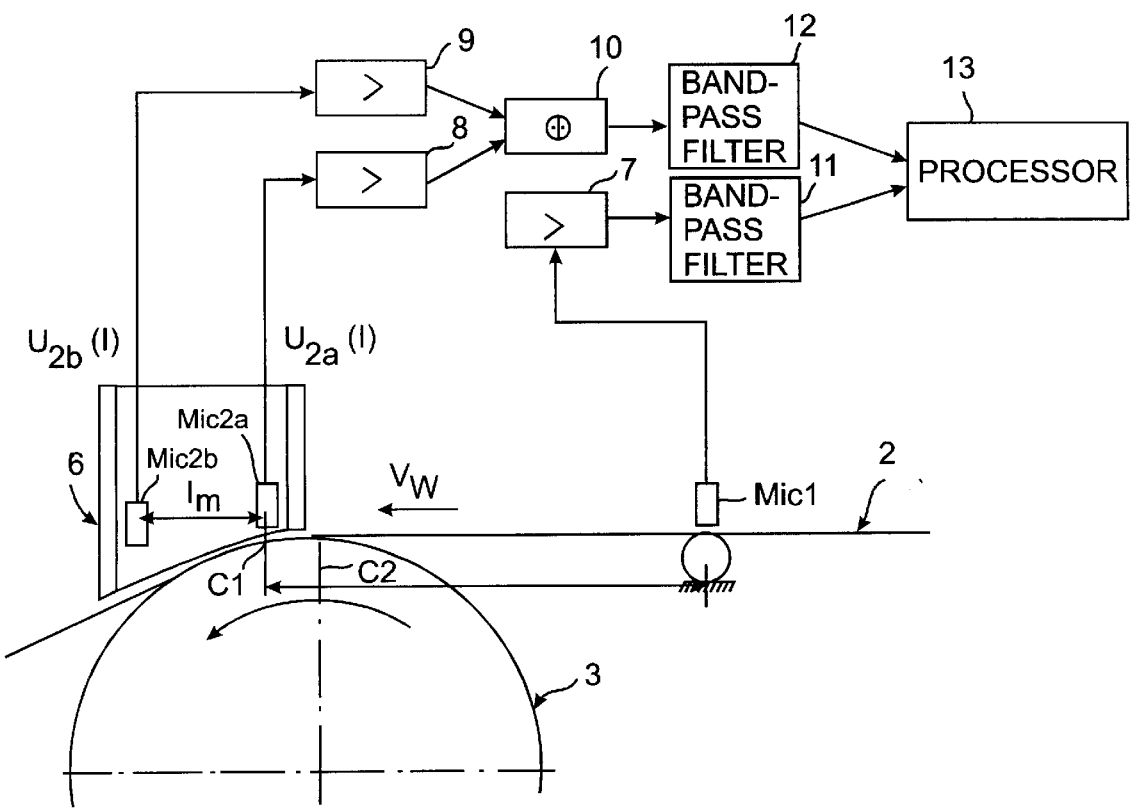
FIG. 2 is a schematic side view of a first embodiment of a measuring system according to the invention.

In accordance with the invention measures are taken to enhance the signal/noise ratio of the correlated signals, particularly in a noisy environment. Therefore, in accordance with a first embodiment of the invention, shown in FIG. 2A, a double channel measuring receiving microphone device is provided at the vicinity of the rotating cylinder 3 to receive the wave propagated along the web, since the lowest signal/noise ratio is obtained at the input of the microphone Mic2 in the prior art system shown in FIG. 1. It is, however, to be noted that more than two pick-up microphones can be provided according to the invention.

In accordance with the invention at least two pick-up ultrasonic microphones Mic2a and Mic2b, being the pick-up elements of the pick-up receivers, are placed a distance $1_m$ from each other the distance being chosen to be a half-wavelength of the ultrasonic wave in air at the centre frequency of the bandwidth of the ultrasonic wave transmitted through the paper web. The microphone Mic2a is located opposite the contact line $C_1$ between the rotating cylinder 3 and the web 2 from which the best radiation into the air of the wave propagated in the web is provided. The microphone Mic2b is located on the side of the microphone Mic2a turned away from the friction head 1. The lateral dimensions of the pick-up microphones Mic2a and Mic2b, and also of the reference microphone Mic1, are at least 10 times less than a wavelength of the ultrasonic wave in the paper web, and all the microphones are placed at a distance from the web less than a wavelength of the ultrasonic wave $s_0$ reradiated by the web into air. Noise is also radiated into the air from the contact line $C_2$ where the web first meets the cylinder 3. This noise should preferably be suppressed as much as possible. Therefore, a noise suppressing shield 6, for instance made of rubber, is provided around the microphones Mic2a and Mic2b shielding them from the noise from the contact line $C_2$ and also from ambient noise. Thus, its outer edge nearest to the contact line $C_2$ is located downstream from this line. The microphones Mic2a and Mic2b are placed close to the internal edge of the shield 6.

The signal part of interest of the ultrasonic wave $v_w$ transmitted through the web to be indicated is the $s_0$ wave signal, which corresponds to the symmetric zero order Lamb waves propagated in the web 2, i.e. the fastest propagating wave.

Thus the principle of the operation is based on a difference of ultrasound velocities in air ($v_a$=343 m/sek) and paper ($v_{s0}$=1.5 to 4 km/sek). The signals at the outputs of the microphones Mic2a and MIC2b are given by:

$$u_{2a}(t) = y_s(t) + y_a(t) + n_{md}(t) + n_{0a}(t)$$

$$u_{2b}(t) = k_s{}^* y_s(t-\Delta t_s) + k_a{}^* y_a(t-\Delta t_a) + k_n{}^* n_{md}(t+\Delta t_a) + n_{0b}(t)$$

where $u_{2a}(t)$ and $u_{2b}(t)$ are the complete wave signals at the output of the microphones Mic2a and Mic2b, respectively, $y_s(t)$ is the $s_0$ wave signal at the output of the microphone Mic2a, $y_a$ is the airborne wave generated by the friction head, $n_{md}$ is the noise propagating along the machine direction at the output of the microphone, $n_{0a}(t)$ and $n_{0b}(t)$ are electronic noise and ambient noise propagating along directions others than the machine direction, $k_s$, $k_a$, and $k_n$ are the coefficients reflecting the asymmetry of the microphones Mic2a and Mic2b for the appropriate waves, $\Delta t_s = l_m/v_{s0}$ is the delay time of the $s_0$ wave between the microphones Mic2a and Mic2b, and $\Delta t_a = l_m/v_a$ is the delay time of airborne waves between the microphones Mic2a and Mic2b propagating along the machine direction.

Due to extensive differences in the ultrasonic velocities in the web and in air, $\Delta t_s \ll \Delta t_a$. Furthermore, $\Delta t_s < t_0$, $t_0 = 1/f_0$, where $f_0$ is the center frequency of the signal spectrum. Therefore, the spectral components with frequencies equal or close to the frequency $f_0$ are approximately:

$$y_s(t) \approx y_s(t-\Delta t_s)$$

$$y_a(t) \approx -y_a(t-\Delta t_a)$$

$$n_{md}(t) \approx -n_{md}(t+\Delta t_a)$$

Then, addition of the signals from the two microphones Mic2a and Mic2b gives the following result:

$$u_2(t) = u_{2a}(t) + u_{2b}(t) = (1+k_s)^* y_s(t) + (1-k_a)^* y_a(t) + (1-k_n)^* n_{md}(t) + n_{0a}(t) + n_{0b}(t)$$

The coefficients $k_s$, $k_a$, $k_n$ are close to 1, which gives approximately:

$$u_2(t) = 2^* y_s(t) + \epsilon_a y_a(t) + \epsilon_n n_{md}(t) + [n_{0a}(t) + n_{0b}(t)]$$

where $\epsilon_a$ and $\epsilon_n$ are much lower than 1, which indicates that the amplitude of the $s_0$ wave signal is amplified twice and the amplitude of the wave propagating in air along the machine direction from the friction head is substatially reduced, like the noise propagating in the machine direction. The electronic noises or the noises arriving from directions different from the machine direction are not suppressed and are added as partially correlated or uncorrelated random processes.

It is to be noted that the distance $l_m$ between the pick-up microphones could be chosen in another way, but then the equations above and the combination of them will be changed. The main feature of the choise of distance is that the term $y_s(t)$ is essentially enhanced and the term $y_a(t)$ essentially reduced at the combination.

Referring now to an embodiment having the pick-up microphones half-wavelength of the airborne ultrasonic wave apart, in order to estimate the velocity of the $s_0$ wave a cross-correlation should be made on the signals from the reference microphone Mic1 and the added signals from the two pick-up microphones Mic2a and Mic2b. The signals are first amplified in respective amplifiers 7, 8, 9. The signals from the amplifiers 8 and 9 are added in an adder 10. The signals from the amplifier 7 and the adder 10 are fed to a processor 13 through bandpass filters 11 and 12, respectively. The processor 13 is provided with a program for performing an automatic time delay measurement in order to obtain the velocity of the wave in the actual paper web.

The delay time is determined from the cross-correlation function. For this purpose two methods are combined, namely, cross-correlation function envelope peak detection for a coarse evaluation and zero-crossing detection of the cross-correlation function Hilbert transform for the accurate measurements. Time diagrams illustrating this technique are given in FIGS. 3A to 3D. This techique is efficient in the case of relatively narrow-band signals, i.e., when a cross-correlation function has an oscillating character.

Figures 3A, 3B, 3C, 3D:
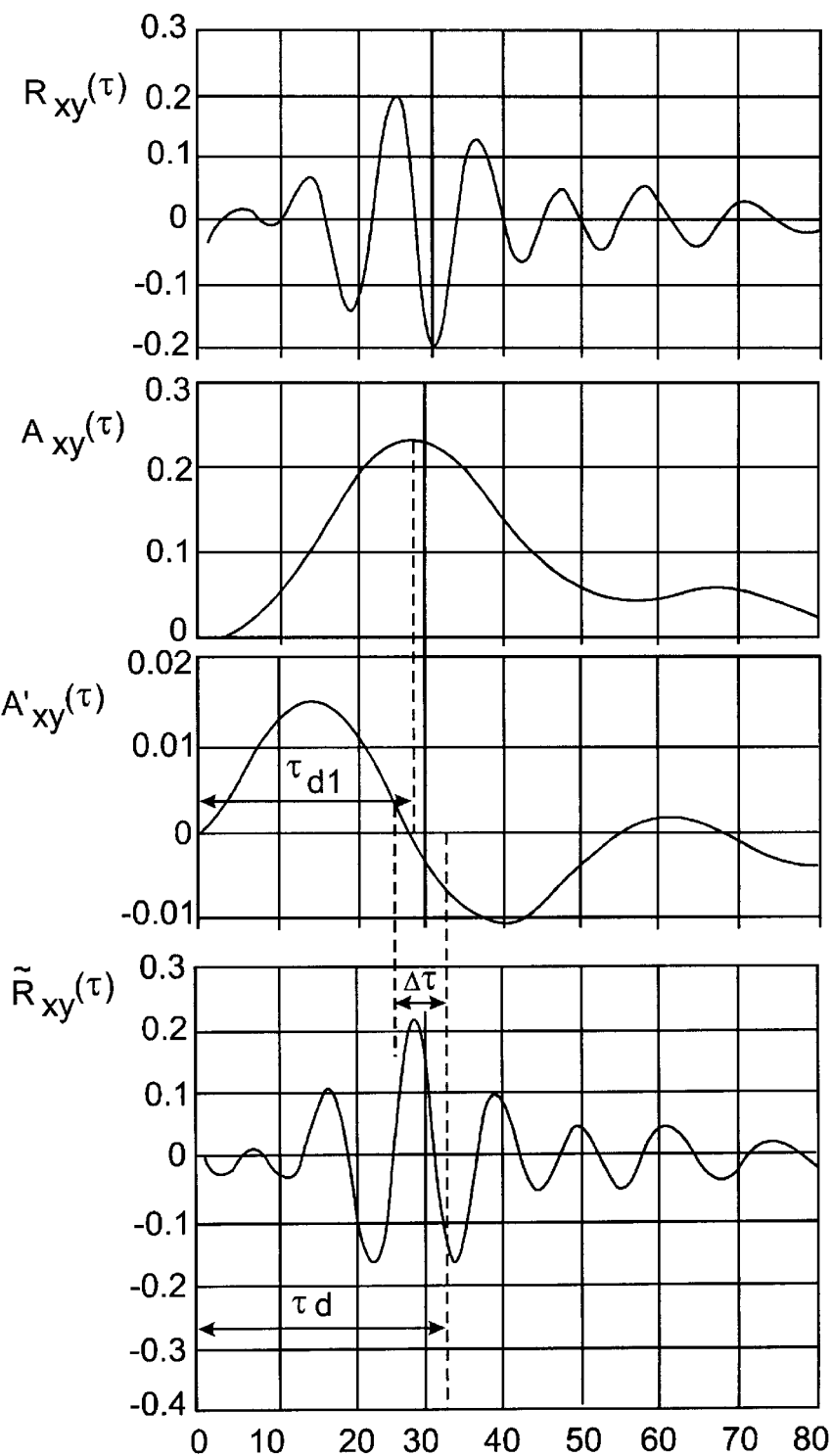
FIGS. 3A to 3D are diagrams of signals provided in different operation steps in searching for the delay time of the ultrasonic wave transmitted through the paper web.

Therefore, as shown in FIG. 3A, a cross-correlation function $\hat{R}_{xy}(\tau)$ between transmitted and received $s_0$ wave signal at the outputs of the receivers Mic1, 7, 11, and Mic2a, Mic2b, 8, 9, 10, 12 is provided $$R_{xy}(\tau) = (1/T)\int^T [x(t) + n_1(t)]^* [2y_a(t+\tau) + \epsilon[y_a(t+\tau) + n_{md}(t+\tau)] + n_2(t+\tau)] dt$$

where T is the signal duration used for calculation, x(t) and y(t+τ) are the signals from the input channel Mic1, 7, 11, and the output channel Mic2a, Mic2b, 8, 9, 10, 12, respectively, and $n_1(t)$ is the noise received by the microphone Mic1 and $n_2(t+\tau)$ is the added noise received by the micropones Mic2a and Mic2b.

A zero-cross of the Hilbert transform of the cross-correlation corresponding to the maximum value of the cross-correlated function is made.

Then, the envelope, as shown in FIG. 3B, of a cross-correlation function Rxy(τ) is obtained by means of the Hilbert transform:

$$A_{xy}(\tau) = \sqrt{[R^2_{xy}(\tau) + \tilde{R}^2_{xy}(\tau)]}$$

(see FIG. 3C), where $$\tilde{R}_{xy}(\tau) = H[R_{xy}(\tau)] = \int_{-\infty}^{\infty} R_{xy}(t)/[\pi^*(\tau-t)] dt$$

is the Hilbert transform of a cross-correlation function $\tilde{R}_{xy}(\tau)$ and shown in FIG. 3D. FIG. 3C shows the detection of the envelope peak shown in FIG. 3B.

In the presence of signals propagating through multiple paths, the cross-correlation function has a few peaks, corresponding to different delays. Then the envelope function can be presented as $$A_{xy}(\tau) = \sum_{i=1}^{N} A_i(\tau - \tau_{di})$$

where $\tau_{d1}, \tau_{d2} \ldots$ are the delays in the corresponding paths. Therefore, in a general case, not just one but a few peaks will be detected. The proper peak is found taking into account a prior knowledge about an expected time of the arrival and usually is the peak closest to the zero instant.

The obtained rough estimate of the delay time $\tau_{d_i}$ is used to produce a window H(t) in a time domain the width of which $\Delta\tau$ is slightly less than half a period of oscillation of the band-limited cross-correlation function $$\Delta\tau < t_0/2.$$

The window is located symmetrically in respect to the determined delay time $\tau_{d_i}$ $$H(t - \hat{\tau}_{d_i}) = \begin{cases} 1, \text{ for } \hat{\tau}_{d_i} - (\Delta\tau/2) \leq t \leq \hat{\tau}_{d_i} + (\Delta\tau/2) \\ 0, \text{ otherwise.} \end{cases}$$

The accurate delay time estimation is obtained from the windowed Hilbert transform $R_w(t)$ of the initial cross-correlation function:

$$R_w(t) = H(t - \hat{\tau}_{d_i}) * \tilde{R}_{xy}(t)$$

The peak value of the envelope function $A_{xy}(\tau)$ corresponds to the peak value of the cross-correlation function $R_{xy}(\tau)$ only in the case of non-dispersive propagation. As it was noticed above, the symmetrical $s_0$ wave used for the measurements propagates without a noticeable dispersion.

On the other hand, the uncertainty in detecting the rough delay time should be less than $t_0/2$. For 35 kHz center frequency, rough delay time uncertainties of as much as $t_0/2 = 14$ $\mu$s can be allowed. Usually this requirement is easy fullfilled and no ambiguity occurs.

The peak values of the cross-correlation function $Rxy(\tau)$ correspond to the zero values of the Hilbert transform $\tilde{R}_{xy}(\tau)$. Hence, the time of signal arrival now can be found sing simple zero-crossing technique (FIG. 3D):

$$R_w(t)_{t=\tau_{d1}} = H(t - \hat{\tau}_{d_i}) * \tilde{R}_{xy}(\tau) = \tau_{d1} = 0.$$

It is worthwhile to remember, that by shifting the window function $H(t)$ to the locations of other envelope peaks $\hat{\tau}_{d_i}$, the accurate delay times of signals propagating through different paths may be automatically determined.

Figure 4:
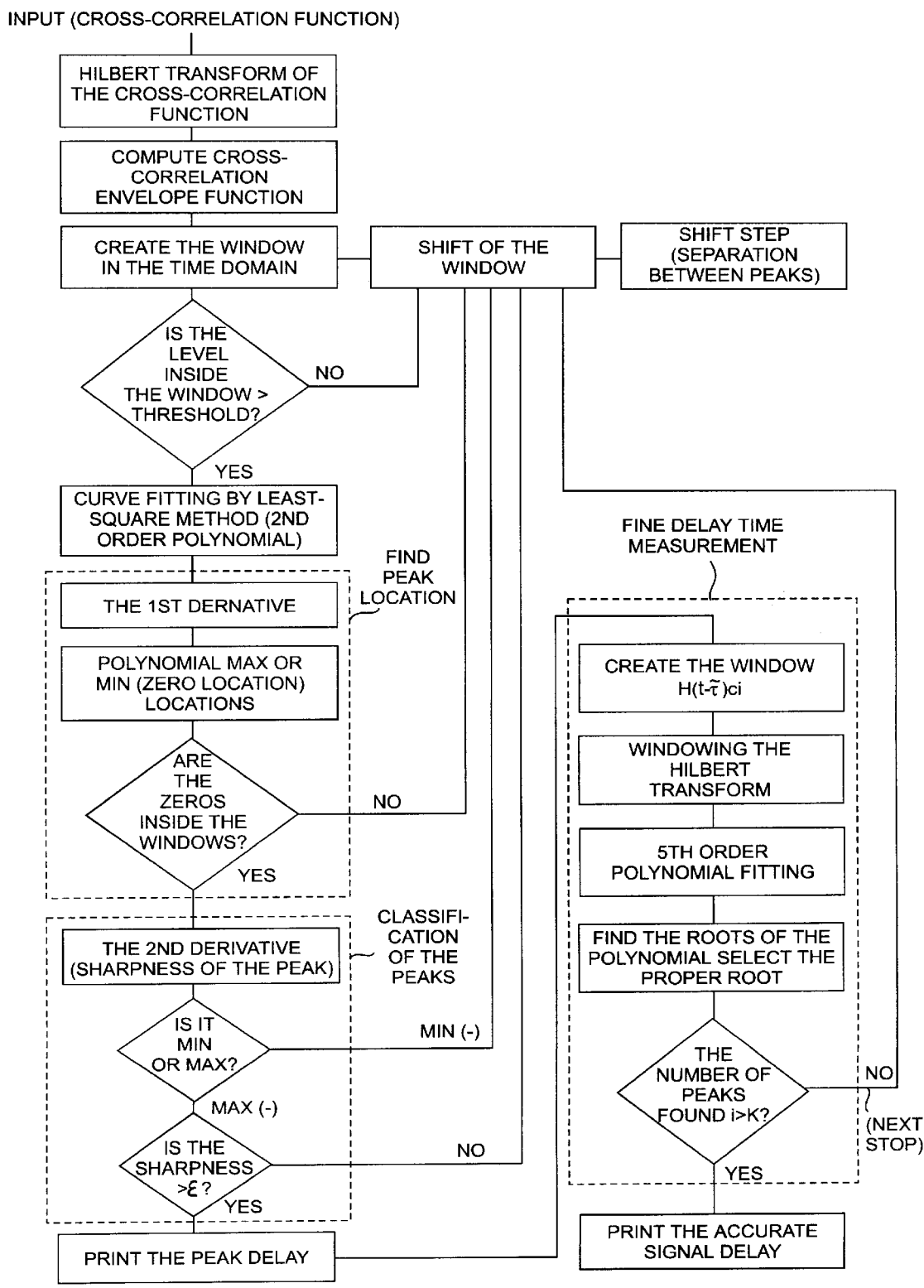
FIG. 4 is a flow chart of the processing operation for providing the delay time of the ultrasonic wave in-plane of the paper web.

A flowchart of a program in the processor 13 for automatically deriving the time delay is shown in FIG. 4 and includes shifting of the window $\Delta\tau$, shown in FIG. 3D, in several steps in order to find the searched time delay $\tau_d$ for the paper web 2.

The algorithm consists of three main stages: cross-correlation envelope function fitting by 2nd order polynomial; finding the peaks; and finding their classification according to a sharpness.

The algorithm starts from the window generation in the time domain. The width of the window is given in terms of sampling points and defines the number of points used in the analysis. The window is shifted step by step in subsequent algorithm loops. The size of this step defines the separation between two neighbouring peaks and can be chosen in such a way that minor peaks caused by a random noise or spurious waves would be ignored.

The cross-correlation envelope function fitting is needed for finding the peak and is performed by the least-square method using the 2nd order polynomial. Such a polynomial can have a positive or negative curvature depending on what kind of local extremity—a peak or a minimum has been found.

Strictly speaking, the 2nd order polynomial fitting always finds a local minimum or maximum independently of how they were created—by delayed signals or by random noise fluctuations. The influence of local fluctuations can be reduced by increasing the width of the window. Then the peaks caused by delayed waves are usually sharper than the other, spurious, peaks.

Therefore, the peak finding procedure consists of the first order derivative calculation, which enables the determination of the locations of all extremities and the 2nd order derivative calculation, which allows sorting them into maximums and minimums and, consequently, selection of the proper peak (or peaks) according to its (or their) sharpness.

The sharpness $\epsilon$ is given by the magnitude of the 2nd derivative of the peak.

The delay time estimate $\tau_{di}$ obtained from this peak is used to generate the window $H(t)$ mentioned above.

The Hilbert transform of the cross-correlation function $\tilde{R}_{xy}(t)$ is multiplied by the windowing function $H(t)$. All these functions are discrete in the time domain. The spacing between two adjacent points is equal to the sampling period $\Delta t_s$. In order to obtain measurement errors less than the signal sampling interval $\Delta t_s$, the segment of the Hilbert transform is fitted using the least-square method by the 5th order polynomial. Then the Equation has five roots, but only the root inside the created window is selected. This root is a fine time delay $t_{di}$ estimation. The wave velocity $v_0 = l_0/t_{di}$, and the tensile stiffness $TSI = c_1 * v_0^2$, where $c_1$ is a dimensionless constant close to 1 depending on Poisson's ratio for the paper. The flowchart in FIG. 4 is believed to be self-explanatory and is therefore not described in further detail.

It is necessary to point out that if the peak of the cross-correlation function caused by the $s_0$-Lamb wave is the biggest, then the envelope function fitting can be omitted and the rough estimate of the peak delay obtained directly from the measured cross-correlation or envelope function. The other steps in the algorithm remain the same.

From a commercial point of view, a measuring system in which all units are located at the same side of a paper web has many advantages. However, in order to implement the single side access approach it is necessary to overcome a lot of problems.

1. According to prior art (FIG. 1), the reference microphone could not be put at the same distance from a signal source as the second channel microphone from a paper web, because both the reference microphone and the signal source had to be located on the same side of the web. For the same reason the reference microphone surface could usually not be perpendicular to a propagation direction of the signal in air, and that caused a significant reduction in a normalized cross-correlation (covariance) function value or a distortion of its shape.

2. The location of the signal source unit and both the reference microphone and the receiving microphone (see prior-art in FIG. 1) for the waves propagated along the web on the same side creates a direct wave propagating in air that is much stronger than in the case of a two-side access, due to no shielding of airborne waves, because then the paper web is not shielding the airborne ultrasonic waves. It reduces a degree of correlation between the transmitted and recieved signals too.

3. The friction head causes an abrasion of the paper and scrapes off fibres which produces dust. If it is placed on the same side of the web as the microphones this dust will be transported to the microphones, which will reduce noticeably their sensitivity and distort their frequency responce, if the same kind of friction heads are used as in the prior art.

Figure 5A:
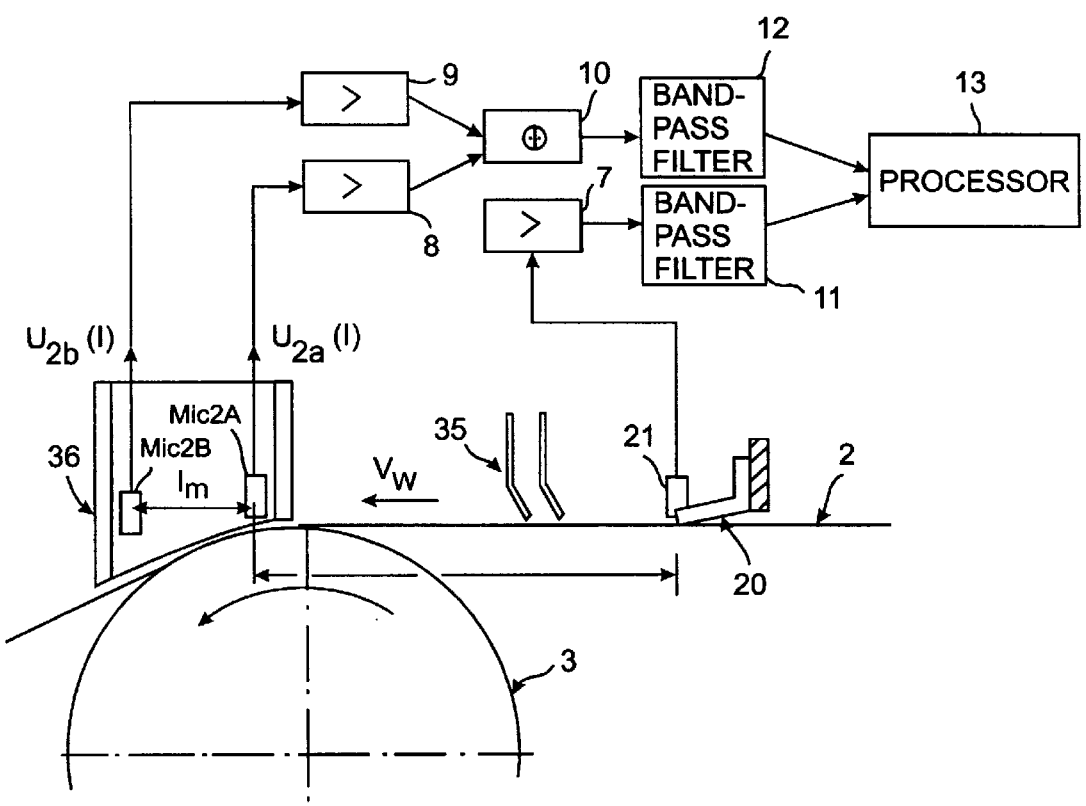
FIG. 5A is a schematic side view of a second embodiment of a measuring system according to the invention.
Figure 5C:
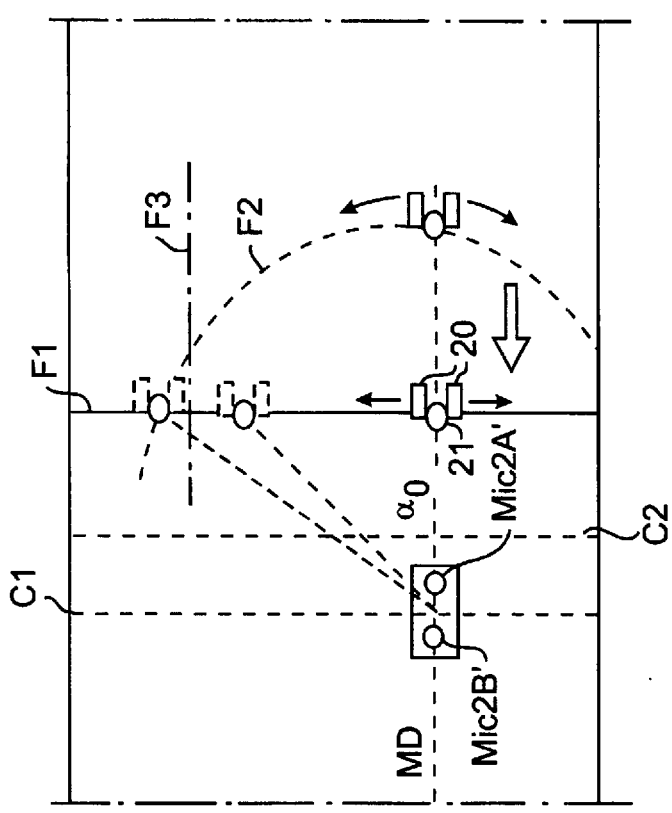
FIGS 5B and 5C illustrate schematic view from above of two embodiments of the system in FIG. 5A having the possibility of measuring the ultrasound velocity in different directions.
Figure 5B:
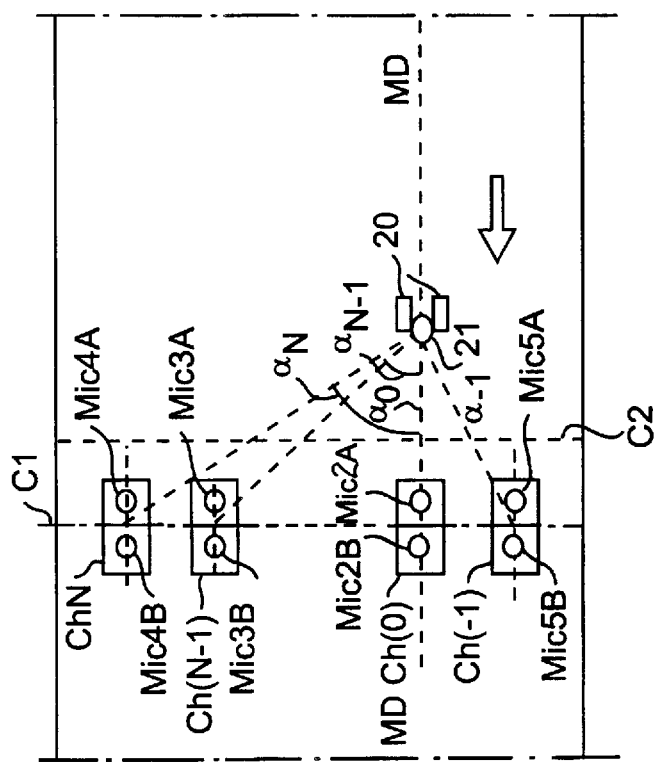

Therefore, a new kind of friction head 20 adapted to a reference microphone 21 is provided according to a further development of the invention illustrated schematically in the second embodiment of the invention shown in FIGS. 5A, 5B, and 5C.

The main feature of the combination of the friction head and the reference microphone is that friction and microphone elements are provided symmetrically to each other. This means that there could be one friction element and an even number of microphone elements provided symmetrically in relation to the friction element such that the microphones in each pair have the same distance to the friction element, or there could be one microphone element and an even number of friction elements placed around the microphone element. The friction elements preferably have a nearly pointlike contact with the paper web.

However, friction elements will cause dust in the environment and measures must be taken to minimize the influence of dust on the microphone(s). Thus, the prefered embodiment is to have a microphone between two pointlike friction elements placed along a line perpendicular to the machine direction, i.e. the moving direction of the web. If more than two friction elements are provided they must all be provided at the side of a line through an ultrasonic sound receiving element of the reference means directed in the machine direction of the moving paper web in order to prevent dust from coming directly on the microphone.

Figure 6A:
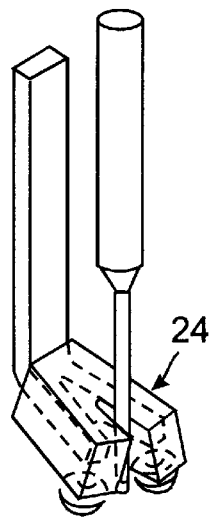
FIGS. 6A, 6B are perspective views of an embodiment of a transmitter/microphone element.
Figure 6B:
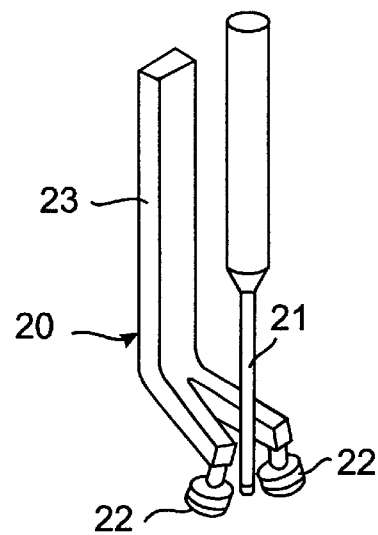

An embodiment of the unit of the friction head and reference microphone is shown in FIGS. 6A and 6B. FIG. 6A shows the actual appearance of the units when a noise shield is provided, and FIG. 6B shows the unit without the noise shield. The new friction head comprises two friction parts 22 placed along a line perpendicular to the machine direction of the paper web. The friction parts are preferably made from a hard alloy material, for instance wolfram carbide. The friction parts 22 are held by a holder 23.

The reference microphone 21 is located between the two friction parts 22 of the friction head 20. The distance D between the friction parts 22 is much less than the wavelength of the ultrasonic wave in the web. Also, the dimensions of the contact area between the friction head 20, and the paper web are less than the wavelength of the ultrasonic wave in the web. Thus, this kind of ultrasonic sound source acts substantially like a two-point-source. The distance between the contact areas and the plane of the reference microphone is comparable with the wavelength in air (for $f_0=40$ kHz, $\lambda_a/2=4.3$ mm).

In order to provide a good correlation between the signals captured by the reference microphone 21 and the microphones Mic2A and Mic2B located at the rotating cylinder 3 (FIG. 5A) it is necessary that the reference microphone 21 is placed as accurately as possible at the same distance from the contact areas between the friction parts 22 and the web. In order to reduce the waves radiated other than by the contact area by the friction parts and transmitted through the air to the reference microphone, a noise shield 24 (FIG. 6A) is placed around the friction parts 22 and held by their holder 23 and is provided with an opening adapted to hold the reference microphone 21 in place.

Each of the two parts of the friction head 22 in FIGS. 6A and 6B are formed as hemispheres. The friction parts of the head 22 are made of hard alloy and comprise tips, covered by a material absorbing ultrasonic waves, for example, a soft rubber contacting the web.

Referring back to FIG. 5A, in order to make an extra shield for the microphones Mic2A and Mic2B, both regarding the airborne noise from the friction head and against the dust from it, a number of shields 35 are provided above the paper web between the microphone 21 and the rotating cylinder 3. Also, as in the embodiment shown in FIG. 2, a noise reducing shield 36, for instance made of rubber, is placed around the microphones Mic2A and Mic2B in order to reduce the noise from the noisy surroundings. The shield 36, having the same function as the shield 6 in the embodiment shown in FIG. 2, has preferably the shape of its lower side adapted to the shape of the paper web when it is transferred over the rotating cylinder 3, as seen from FIG. 5A (as well as from FIG. 2).

The method above has been described for measurement of the time delay in the machine direction and this will give the tensile stiffness index $TSI_{MD}$ in the machine direction of the paper machine. The friction head 20, the microphones 21, Mic2A and Mic2B are then located in line with the machine direction. However, as mentioned in the introductory part of the specification, the tensile stiffness index $TSI_{CD}$ in the cross direction of the paper machine, and in directions between $TSI_{MD}$ and $TSI_{CD}$, are also needed in order to calculate the anisotropy ratio and the tensile stiffness orientation. An embodiment for providing also these quantities will now be described with reference to FIGS. 5B and 5C, even though the same feature naturally can also be provided for the embodiment shown in FIG. 2.

As is apparent from FIG. 5B, several sets of microphones Mic3A, Mic3B; Mic4A, Mic4B etc are shown located parallel to each other and oblique to the microphone 21 in relation to the machine direction (the respective angular directions $\alpha_{N-1}$, $\alpha_N$ etc), such that each microphone Mic3A, Mic4A is situated tangentially in the same location above the rotating cylinder 3 as the microphone Mic2A. The delay time of the symmetrical Lamb wave propagating in that oblique direction, $\alpha_{N-1}$, $\alpha_N$ etc, is measured in the same way as described above for the ultrasonic Lamb wave propagation in the machine direction taking account of the somewhat longer propagation path for each set.

Instead of providing an array of receiving pick-up microphone sets only one set need be provided, said set being movable along the cylinder above the web so as to be placed in different oblique positions, i.e. scanning along the line C1. In this instance it is important to place the set of microphones in accurately precise positions above the paper web (same distance to the web and along line C1) in order to have the same measuring conditions for each measured oblique setting (not shown in a separate figure, however the pick-up microphone set will be placed in the same way as shown in FIG 5B).

Another embodiment, shown in FIG. 5C has only one pick-up microphone set Mic2A', Mic2B' and moves, as a unit, friction head 20 and reference microphone 21 across the web, for instance along a straight line F1 parallel to the line C1, as shown, and to derive the delay time for the $s_0$ wave for a chosen amount of settings of the unit 20,21 having different angular positions in relation to the pick-up microphone set. It is also possible to move the friction-head/microphone set 20,21 along a curved line F2 (dashed), or to provide the velocity measurement along the machine direction separately and the measurements in the oblique directions along a line F3 (dot/dashed) perpendicular to the line C1.

It should be noted that even for the embodiments having scanning elements along a line and one element constantly in the same position, each measuring result is provided having both kinds of elements in the same position in relation to each other during the time it takes to get the measuring result.

Many different kinds of numerical methods may be used to provide a quite precise estimation about the $s_0$ wave rate in the cross direction of the paper web. One method is to fit the measured $s_0$ wave rates for the different oblique positions in some kind of periodic function, e.g. the function for an ellipse or some kind of Fourier serie.

Example in which a trigonometric first order Fourier series is used:

We assume that the ultrasonic velocity of the $s_0$ wave has been measured in three different directions and these three different values are used for determining constants a0, a1 and b1. The constants are then inserted in the following formula:

$$f(\alpha)=a0+a1*\cos 2\alpha+b1*\sin 2\alpha \quad (1)$$

The estimated velocity is also dependent on formula 2:

$$f(x)=k1*x+k2 \text{ (where } x=f(\alpha)max/f(\alpha)min) \quad (2)$$

The constants k1 and k2 are known. A combination of the functions 1 and 2 will give the following function which determines the $s_0$ wave velocity in the cross direction ($\alpha=90°$).

$$v(CD)=f(x)*(a0-a1) \quad (3)$$

By changing the constants k1 and k2 it is possible to get the velocity in any direction from the formula 4:

$$v(\alpha,max/min)=(k1(\alpha)*x+k2(\alpha))*(a0+a1*\cos 2\alpha+b1*\sin 2\alpha) \quad (4)$$

Figure 5D:
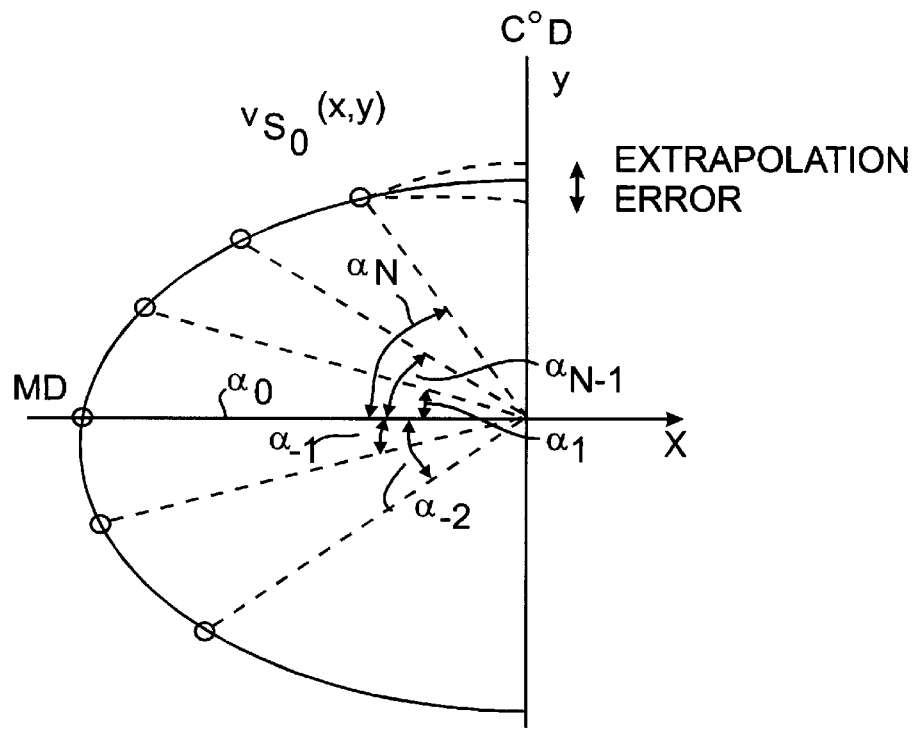
FIG. 5D illustrates a graph to provide an extrapolated value of the ultrasound velocity in the cross direction.

Another advantageable way to derive the velocity of the $s_0$ wave in the cross direction from the results from the different settings of the friction-head/reference-microphone and the pick-up microphones in relation to each other is to set the measuring results of the $s_0$ wave rates in a coordinate system, having the rate in the machine direction along the X-axis and the rate in the cross direction of the web along the Y-axis, in relation to the respecive angular deviation $\alpha_{N-1}$, $\alpha_N$ etc of each set to the machine direction in the way shown in FIG. 5D. A curve is drawn through the different measuring results and extrapolated to cut the Y-axis in order to provide the velocity of the $s_0$ wave in the web in the cross direction. A small extrapolation error is unavoidable but is minimized by having a lot of settings of the friction-head/reference-microphone in relation to the pick-up microphones, the more the better.

The same extrapolation technique as shown in FIG. 5C can be used also for the embodiments shown in FIG. 5D.

While the invention has been described with reference to specific embodiments, it will be understood by those skilled in the art that various changes may be made and equivalents may be substituted for elements thereof without departing from the scope of the invention as apparent from the Claims. In addition, modifications may be made without departing from the essential teachings of the invention. For instance, more than two pick-up microphones could be provided at the rotating cylinder.

We claim:

1. A system for measuring an ultrasonic wave at least partially passing through a moving paper web comprising:

means for generating a noise type ultrasonic wave in the paper web at an excitation point;

reference ultrasonic wave receiving means for receiving the ultrasonic wave reradiated from the paper web into the air from the excitation point, said reference ultrasonic wave receiving means being free from contact with said moving paper web;

at least two pick-up ultrasonic wave receiving means for receiving the ultrasonic wave generated by the ultrasonic wave generating means and reradiated by the paper web, said pick-up ultrasonic wave receiving means being free from contact with said moving paper web;

processing means to combine outputs from the pick-up ultrasonic wave receiving means such that those portions of the outputs which are dependent on velocity of the ultrasonic wave propagating in the paper web are enhanced, and those portions of the outputs which are dependent on the ultrasonic wave propagating in air are reduced at the combination of outputs; and computing means for processing the outputs from said reference ultrasonic wave receiving means and from said processing means, and determining a delay time between these outputs.

2. The system according to claim 1, wherein said reference ultrasonic wave receiving means and said pick-up ultrasonic wave receiving means have lateral dimensions which are at least 10 times less than a wavelength of the ultrasonic wave in the paper web, and said reference ultrasonic wave receiving means and said pick-up ultrasonic wave receiving means are placed at a distance from the paper web which is less than a wavelength of the ultrasonic wave reradiated by the paper web into the air.

3. The system according to claim 2, wherein a distance between adjacent pick-up ultrasonic wave receiving means in a plane parallel to the paper web is substantially equal to half of the wavelength of the ultrasonic wave, said wavelength measured in air at the center frequency of a band width of the ultrasonic wave.

4. The system according to claim 1, wherein said means for generating the ultrasonic wave, said reference ultrasonic wave receiving means, and said pick-up ultrasonic wave receiving means are located on one side of the paper web.

5. The system according to claim 1, wherein said pick-up ultrasonic wave receiving means are placed along a straight line in order to obtain a time between generation of the ultrasound wave propagating in the paper web and the reradiation of the ultrasonic wave at said pick-up ultrasonic wave receiving means in order to derive a Tensile Stiffness Index in the direction of a movement of the paper web.

6. The system according to claim 1, wherein said pick-up ultrasonic wave receiving means can be oriented obliquely in relation to said reference receiving means at different angles to the direction of movement of the paper web in order to obtain a time between generation of the ultrasound wave propagating in the paper web and the reradiation of the wave at the pick-up ultrasonic wave receiving means in order to derive a Tensile Stiffness Index in a direction which is oblique to the direction of movement of the paper web.

7. The system according to claim 6, wherein results from measurements taken at several oblique directions are combined to obtain a Tensile Stiffness Index in a cross direction relative to the direction of movement of the paper web.

8. The system according to claim 1, wherein said pick-up ultrasonic wave receiving means are located above and close to a rotating cylinder of a paper-making machine carrying the paper web and are positioned along the direction of movement of the paper web, a first pick-up receiving means located at a line defined at a point where said paper web first contacts a surface of said cylinder, and a second pick-up receiving means located downstream from said line relative to the direction of movement of the paper web.

9. The system according to claim 1, wherein a first shield is placed between said reference ultrasonic wave receiving means and said pick-up ultrasonic wave receiving means for reducing an amplitude of an airborne ultrasonic wave propagating from said ultrasonic wave generating means to said pick-up ultrasonic wave receiving means.

10. The system according to claim 1, wherein at least said pick-up ultrasonic wave receiving means are placed close to a rotating cylinder of a paper making machine carrying the paper web and are located inside a second shield, an outer edge of said second shield is located downstream relative to the direction of movement of the paper web from a line defined at a point where the moving paper web first contacts a surface of the cylinder, and said pick-up ultrasonic wave receiving means are placed close to an inside edge of said shield.

11. The system according to claim 1, wherein computing means are utilized to determine a delay time as a zero-cross of the Hilbert transform of a cross-correlation function between outputs of said reference receiving means and said processing means, corresponding to the maximum value of the cross-correlation function.

12. The system according to claim 11, wherein a Hilbert window is created in a time domain and is shifted until a peak location in time of the cross-correlation function is found and a sharp peak is derived.

13. The system according to claim 1, wherein said ultrasonic wave generating means comprises dry friction elements in contact with the moving paper web, a contact dimension of said generating means are much less than a wavelength of the ultrasonic wave in the paper web, and said reference ultrasonic wave receiving means is placed in close vicinity of two of said friction elements.

14. The system according to claim 5, wherein said straight line is in the direction of movement of the paper web.

15. The system according to claim 10, wherein said second shield comprises a rubber cylinder.

* * * * *